US006897950B2

(12) United States Patent
Li et al.

(10) Patent No.: US 6,897,950 B2
(45) Date of Patent: May 24, 2005

(54) LASER TWEEZERS AND RAMAN SPECTROSCOPY SYSTEMS AND METHODS FOR THE STUDY OF MICROSCOPIC PARTICLES

(75) Inventors: Yong-Qing Li, Greenville, NC (US); Mumtaz A. Dinno, Greenville, NC (US)

(73) Assignee: East Carolina University, Greenville, NC (US)

( * ) Notice: Subject to any disclaimer, the term of this patent is extended or adjusted under 35 U.S.C. 154(b) by 6 days.

(21) Appl. No.: 10/196,649

(22) Filed: Jul. 16, 2002

(65) Prior Publication Data

US 2004/0012778 A1 Jan. 22, 2004

(51) Int. Cl.[7] .................................................. G01J 3/44
(52) U.S. Cl. ...................................................... 356/301
(58) Field of Search ......................................... 356/301

(56) References Cited

U.S. PATENT DOCUMENTS

| | | | |
|---|---|---|---|
| 6,055,106 A | 4/2000 | Grier et al. | 359/566 |
| 6,067,859 A | 5/2000 | Kas et al. | 73/800 |
| 6,100,975 A | 8/2000 | Smith et al. | 356/301 |
| 6,139,831 A | 10/2000 | Shivashankar et al. | 424/82.05 |
| 6,159,749 A | 12/2000 | Liu | 436/527 |
| 6,373,567 B1 | 4/2002 | Wise et al. | 356/301 |

FOREIGN PATENT DOCUMENTS

JP         2001-14374     *  5/2001  ............ G01N/1/02

OTHER PUBLICATIONS

Lankers, M., et al., "Raman and Florescence Spectra of Single Optically Trapped Microdroplets in Emulisions" Applied Spectroscopy vol. 48, No. 9, 1994, pp. 1166–1168.

Ajito, K., "Combined Near–Infrared Raman an Microprobe and Laser Trapping System: Application to the Analysis of a Single Organic Microdroplet in Water", Applied Spectroscopy, vol. 52, No. 3, 1998, pp. 339–342.

Afzal, Robert, "Optical tweezers using a diode laser", Rev. Sci., Instrum. 63(4), Apr. 1992, pp. 2157–2163.

Ajito et al.; "Near–infrared Raman spectroscopy of single particles" *trends in analytical chemistry* 20:5 255–262 (1002).

A. Ashkin; "Acceleration and Trapping of Particles by Radiation Pressure" *Physical Review Letters* 24:4 156–159 (1970).

Ashkin et al.; "Observation of a single–beam gradient force optical trap for dielectric particles" *Optics Letters* 11:5 288–290 (1986).

(Continued)

*Primary Examiner*—F. L. Evans
*Assistant Examiner*—Kara Geisel
(74) *Attorney, Agent, or Firm*—Myers Bigel Sibley & Sajovec

(57) ABSTRACT

Methods and systems for studying microscopic particles are provided. An optical trap for a selected microscopic particle can be formed with a laser beam at a first power level. The laser beam can have a variable power level associated therewith. The variable power level can be increased to a second power level. The laser beam at the second power level can produce Raman scattering signals. The second power level can provide sufficient excitation energy to the selected microscopic particle to produce Raman scattering signals and the second power level is higher than the first power level. A Raman spectrum can be detected from the Raman scattering signals produced by the laser beam at the second power level.

34 Claims, 17 Drawing Sheets

OTHER PUBLICATIONS

Ashkin et al.; "Optical trapping and manipulation of single cells using infrared laser beams" *Nature* 330:24 769–771 (1987).

Baraga et al.; "Rapid Near–Infrared Raman Spectroscopy of Human Tissue with a Spectrograph and CCD Detector" *Applied Spectroscopy* 46:2 187–190 (1992).

Bell et al.; "Analysis of luminescent samples using subtracted shifted Raman spectroscopy" *Analyst* 123 1729–1734 (1998).

Brennan III et al.; "Near–Infrared Raman Spectrometer Sytems for Human Tissue Studies" *Applied Spectroscopy* 51:2 201–208 (1997).

Furukawa et al.; "Optical trapping of metallic particles by a fixed Gaussian beam" *Optics Letters* 23:3 216–218 (1998).

Gogotsi et al.; "Cyclic nanoindentation and Raman microspectroscopy study of phase transformation in semiconductors" *J. Mater. Res.* 15:4 871–879 (2000).

He et al.; "Direct Observation of Transfer of Angular Momentum to Absorptive Particles from a Laser Beam with a Phase Singularity" *Physical Review Letters* 75:5 826–829 (1995).

Hoffman et al.; "Substitutional carbon in germanium" *Physical Review B* 55:17 167–173 (1997).

Li et al.; "Coherent transient amplification in inhomogenously broadened ribidium atoms by diode–laser frequency switching" *Optics Letters* 21:13 982–984 (1996).

Li et al.; "Surface enhanced resonance Raman spectroscopy of rhodamine 6G adsorbed on silver electrode in lithium batteries" *Chemical Physics Letters* 330 249–254 (2000).

Mosier–Boss et al.; "Fluorescence Rejection in Raman Spectroscopy by Shifted–Spectra, Edge Detection, and FFT Filtering Techniques" *Applied Spectroscopy* 49:5 630–638 (1995).

Neddersen et al.; "Laser Ablation of Metals: A New Method for Preparing SERS Active Colloids" *Applied Spectroscopy* 47:12 1959–1964 (1993).

Neuman et al.; "Characterization of Photodamage to *Escherichia coli* in Optical Traps" *Biophysical Journal* 77 2856–2863 (1999).

Nie et al.; "Probing Single Molecules and Single Nanoparticles by Surface–Enhanced Raman Scattering" *Science* 275 1102–1106 (1997).

O'Neil et al.; "Three–dimensional optical confinement of micron–sized metal particles and the decoupling of the spin and orbital angular momentum within an optical spanner" *Optics Communications* 185 139–143 (2000).

Roosen et al.; "The TEM01 Mode Laser Beam—A Powerful Tool for Optical Levitation of Various Types of Spheres" *Optics Communications* 26:3 432–436 (1978).

Sasaki et al.; "Optical trapping of a metal particle and a water droplet by a scanning laser bean" *Appl. Phys. Lett.* 60:7 807–809 (1992).

Sato et al.; "Optical trapping of microscopic metal particles" *Optics Letters* 19:22 1807–1809 (1994).

Schuster et a.; "Single–cell analysis of bacteria by Raman microscopy; spectral information on the chemical composition of cells and on the heterogenity in a culture" *Journal of Microbiological Methods* 42 29–38 (2000).

Shreve et al.: "Effective Rejection of Fluorescence Interference in Raman Spectroscopy Using a Shifted Excitation Difference Technique" Applied Spectroscopy 46:4 707–711 (1992).

Sureau et al.; "An Ultraviolet Micro–Raman Spectrometer: Resonance Raman Spectroscopy within Single Living Cells" *Applied Spectroscopy* 44:6 1047–1051 (1990).

Karel Svoboda; "Biological Applications of Optical Forces" *Annu. Rev. Biophys. Biomol. Struct.* 23 247–285 (1994).

Wood et al.; "Micro–Raman characterization of the R to T state transition of haemoglobin within a single living erythrocyte" *Biochimica et Biophysica Acta* 1539 58–70 (2001).

* cited by examiner

LASER TWEEZERS AND RAMAN SPECTROSCOPY SYSTEMS AND METHODS FOR THE STUDY OF MICROSCOPIC PARTICLES

BACKGROUND OF THE INVENTION

1. Field of the Invention

The present invention relates to laser tweezers and Raman spectroscopy (LTRS) systems and methods.

2. Description of the Related Art

Detection and identification of microscopic particles using micro-Raman spectroscopy has been used in various scientific disciplines, including materials science, biology and medicine. G. Turrell and J. Corset, *Raman microscopy*, (Academic Press, London, 1996). J. H. Laserna, *Modern techniques in Raman spectroscopy*, (John Wiley & Sons, Chichester, 1996). As an analytical tool, micro Raman spectroscopy uses a focused laser beam to illuminate particles, and the resulting scattered light is detected and analyzed. The incident light on the sample must be administered at an energy level sufficient to excite molecules in the sample to produce inelastic scattering. Even when inelastic scattering occurs, most of the scattered light is elastically scattered, and is called "Rayleigh scatter." This light is the same wavelength as the incident light. However, some of the light is inelastically scattered due to the excitation of molecules in the sample, resulting in scattered light having a wavelength that is different from the incident light. The inelastically scattered light spectrum is called a Raman spectrum. The molecular composition and structure information of the particles can be obtained from positions, intensities, and line-widths of the Raman peaks in the spectra.

When particles, such as colloid particles and motile biological cells, are dispersed in a liquid, the conventional micro-Raman spectroscopy becomes less effective because the particles will randomly move in and out of the illuminating micro-probe beam due to Brownian motion. In such a case, the particles under study have to be immobilized with either physical or chemical methods.

Optical tweezers are used to trap particles by exploiting the properties of momentum associated with light. When light passes through a fluid medium, the optical path is bent by refraction in the fluid material. The bending of the light path corresponds to a change in momentum of the light. If a dielectric particle is suspended in a fluid media of lower refractive index, the light path bends as shown in FIG. 1. The bending of the light path 11 corresponds to a transfer of momentum from the light to the refracting dielectric particle 13. The transfer of momentum exerts a force, which is capable of holding or manipulating the motion of the particle 13.

Researchers have combined various spectroscopic techniques, including adsorption, fluorescence, and Raman spectroscopy, with optical tweezers to characterize various types of samples. In laser tweezers/Raman spectroscopy (LTRS) systems, the same laser is typically used to both trap a sample particle and to excite molecules in the sample to produce a Raman spectrum. For example, a LTRS system was developed to study single trapped polystyrene beads with a power of 80 mW from a Ti:Sapphire laser. See K. Ajito and K. Torimitsu, Trends Anal. Chem. 20, 255 (2001). The same Ti:Sapphire laser was used for both trapping and excitation.

However, obtaining Raman measurements of small particles may cause severe photodamage, particularly to living cells. Relatively small particle samples confined to a small space by laser tweezers require a high-intensity excitation in order to obtain a Raman measurement. Such high-intensity excitation over time can cause severe photodamage and destroy the sample. For example, photodamage to single *Eschericia coli* cells in an optical trap were observed after a few minutes of optical trapping with a continuous wave (cw) laser. K. Neuman, E. H. Chadd, G. F. Liou, K. Bergman, and S. M. Block, Biophys. J. 77, 2656 (1999).

On the other hand, Raman spectroscopy of small particle samples such as single living cells could prove useful for providing information about species, structures, and molecular conformation with the particles being studied. Raman spectroscopy may provide a fingerprint for the identification of microscopic particles.

Raman spectroscopy and optical trapping may also be useful in studying particles having a high index of refraction and high coefficients of absorption. Living biological cells and microdroplets are typically relatively transparent and have a low relative index of refraction. Stable trapping with a single Gaussian beam may be obtained with such particles, in part, because any force produced by scattered light is minimal in comparison to the gradient force produced by the change in momentum of the laser through the surrounding fluid. However, for particles having a high index of refraction and high coefficients of reflection and absorption, such as metallic particles, it is more difficult to achieve stable trapping with a single Gaussian beam. The gradient force produced by the laser may be small in comparison with the enlarged scattering force. Such a scattering force generally points in the direction of the incident laser beam and tends to repulse the particles from the laser beam. A. Ashkin, J. M. Dziedzic, J. E. Bjorkholm, and S. Chu, Opt. Lett. 11, 228–290 (1986). A. Ashkin, J. M. Dziedzic and T. Yamane, Nature, 330, 769–771 (1987). K. Svoboda and S. M. Block, Annu. Rev. Biophys. Biomol. Struc. 23, 247–284 (1994).

Several schemes have been developed to confine metal particles and absorptive particles, including techniques using a two-dimensional trapping by a $TEMO_{01}$-mode laser beam (A. Ashkin and J. M. Dziedzic, Appl. Phys. Lett., 24, 432 (1974). G. Roosen and C. Imbert, Opt. Commun. 26, 432 (1978).), a high-order Laguerre-Gaussian beam (H. He, M. E. J. Friese, N. R. Heckenberg, and H. Rubinsztein-Dunlop, Phys. Rev. Lett. 75, 826–829 (1995). A. T. O'Neil and M. H. Dadgett, Opt. Commun., 185, 139–143 (2000).) and a circularly scanning beam (K. Sasaki, M. Koshioka, H. Misawa, N. Kitamura, and H. Masuhara, Appl. Phys. Lett. 60, 807–809 (1992).). These methods rely on the repulsive scattering force to trap the non-transparent particles in the dark central minimum of a doughnut-shaped beam. Metal particles have also been confined to two-dimensions with a fixed Gaussian beam at an off-axial position based on the attractive force arising from a creeping wave (H. Furukawa and I. Yamaguchi, Opt. Lett. 23, 216–219 (1998)), or at an off-focus position when the laser beam focus is located near the bottom of the particle (Shunichi Sato, Yasunori Harada, and Yoshio Waseda, Opt. Lett. 19, 1807–1809 (1994).). However, these techniques do not propose the combination of Raman spectroscopy with optical trapping for highly refractive and non-transparent particles.

Therefore, there remains a need to develop LTRS systems and methods for optically trapping a sample and subsequently performing Raman spectroscopy on the sample while minimizing photodamage to the sample and/or for studying particles having a high index of refraction and high coefficients of absorption.

SUMMARY OF THE INVENTION

In certain embodiments according to the invention, methods for studying selected microscopic particles are provided.

An optical trap for a selected microscopic particle is formed with a laser beam at a first power level. The laser beam has a variable power level associated therewith. The variable power level is increased to a second power level, and the laser beam at the second power level produces Raman scattering signals. The second power level provides sufficient excitation energy to the selected microscopic particle to produce Raman scattering signals, and the second power level is higher than the first power level. A Raman spectrum is detected from the Raman scattering signals produced by the laser beam at the second power level.

In other embodiments according to the invention, systems for studying selected microscopic particles are provided. A diode laser is provided for producing a laser beam having at least a first and second power level. The laser beam at the first power level is sufficient for optically trapping a selected microscopic particle immersed in a aqueous solution. The laser beam at the second power level provides sufficient excitation energy to the selected microscopic particle to produce Raman scattering signals for a Raman spectrum. The second power level is greater than the first power level. A beam splitter is positioned to selectively direct the laser beam in a first direction and to selectively direct the Raman scattering signals radiating from the selected microscopic particle in a second direction. A container for containing the selected microscopic particle immersed in the aqueous solution is position to receive the laser beam in the first direction. A Raman spectrograph detector is positioned to receive the Raman scattering signals in the second direction.

In still further embodiments according to the invention, methods for studying microscopic particles are provided. An optical trap is formed for optically trapping a selected microscopic particle with a laser beam. The selected microscopic particle has a proximal side and a distal side to a source of the laser beam. The beam is focused near the distal side of the selected microscopic particle. Raman scattering signals are produced with the laser beam, and a Raman spectrum is detected from the Raman scattering signals produced by the laser beam.

DETAILED DESCRIPTION OF THE INVENTION

Figure 1:
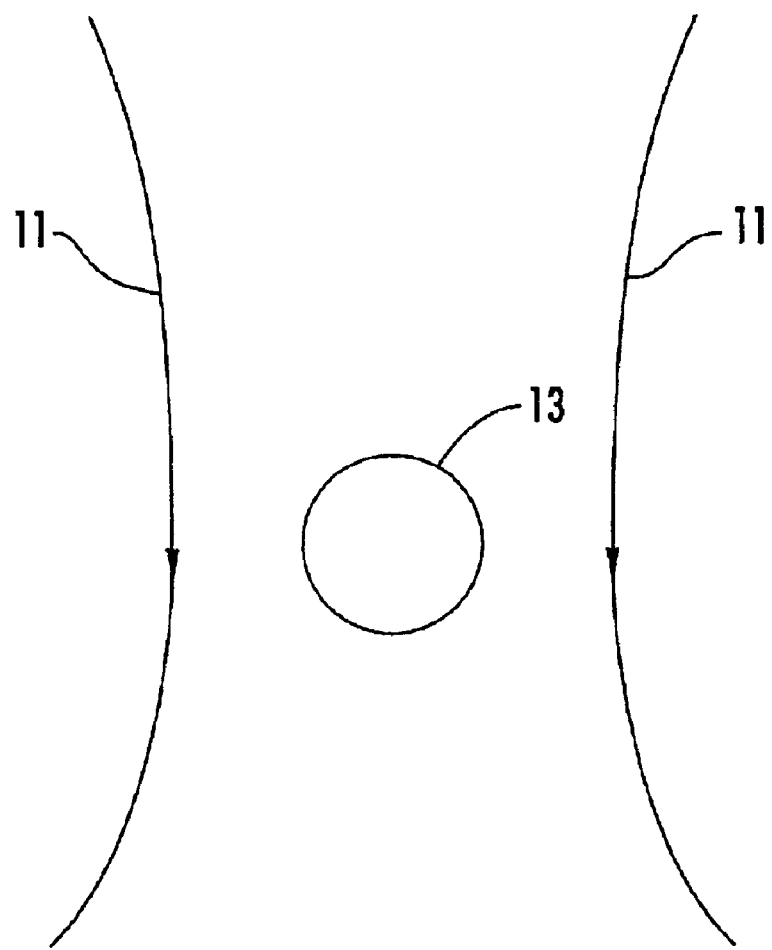
FIG. 1 is a schematic drawing illustrating an optically trapped particle.

The present invention now will be described more fully hereinafter with reference to the accompanying drawings, in which various embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the relative sizes of elements may be exaggerated for clarity. Like reference numerals in the drawings denote like members.

All publications, patent applications, patents, and other references mentioned herein are incorporated by reference in their entirety.

In certain embodiments, methods for studying selected microscopic particles are provided. An optical trap for a selected microscopic particle is formed with a laser beam at a first power level. The laser beam has a variable power level associated therewith. The variable power level is increased to a second power level, and the laser beam at the second power level produces Raman scattering signals. The second power level provides sufficient excitation energy to the selected microscopic particle to produce Raman scattering signals, and the second power level is higher than the first power level. A Raman spectrum is detected from the Raman scattering signals produced by the laser beam at the second power level.

In some embodiments according to the invention, systems for studying selected microscopic particles are provided. A diode laser is provided for producing a laser beam having at least a first and second power level. The laser beam at the first power level is sufficient for optically trapping a selected microscopic particle immersed in a fluid medium such as an aqueous solution. The laser beam at the second power level provides sufficient excitation energy to the selected microscopic particle to produce Raman scattering signals for a Raman spectrum. The second power level is greater than the first power level. A beam splitter is positioned to selectively direct the laser beam in a first direction and to selectively direct the Raman scattering signals radiating from the selected microscopic particle in a second direction. A container for containing the selected microscopic particle immersed in the aqueous solution is position to receive the laser beam in the first direction. A Raman spectrograph detector is positioned to receive the Raman scattering signals in the second direction.

In still further embodiments according to the invention, methods for studying microscopic particles are provided. An optical trap is formed for optically trapping a selected microscopic particle with a laser beam. The selected microscopic particle has a proximal side and a distal side to a source of the laser beam. The beam is focused near the distal side of the selected microscopic particle. Raman scattering signals are produced with the laser beam, and a Raman spectrum is detected from the Raman scattering signals produced by the laser beam.

Embodiments of the invention can be used to study microscopic particles ranging from about 10 µm, 5.0 µm, 1.0 µm, or 0.5 µm to about 0.4 µm, 0.3 µm, 0.2 µm, or 0.1 µm. As used herein, the term "optical trap" refers to the spatial manipulation of a particle using one or more light sources.

Figure 2:
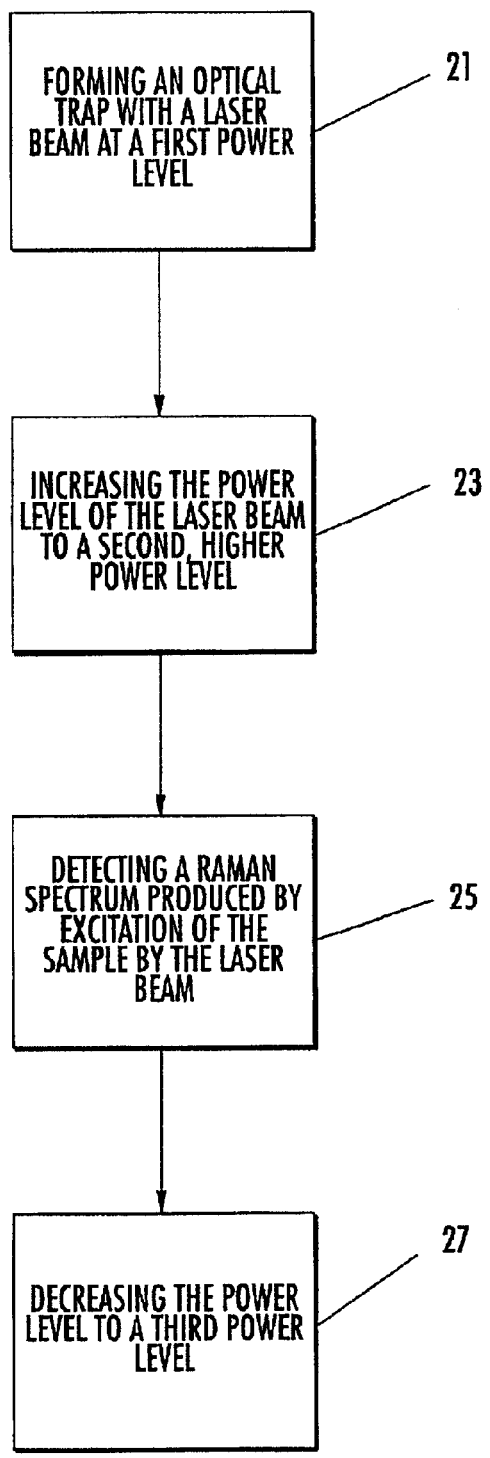
FIG. 2 is a flowchart illustrating operations that can be carried out according to embodiments of the present invention.

FIG. 2 is a flowchart illustrating operations that can be carried out according to embodiments of the present invention. An optical trap is formed with a laser beam at a first power level (Block 21). The laser beam has a variable power level that can be adjusted, for example, by an operator. The variable power level of the laser beam is increased to a second, higher power level (Block 23). The second power level is greater than the first power level and provides sufficient excitation energy to the selected microscopic particle to produce a Raman spectrum. The Raman spectrum is then detected, for example, by an imaging spectrograph (Block 25). After the Raman spectrum is produced, the power level of the laser can be decreased to a third power level (Block 27).

The first and third power levels are preferably sufficient to form an optical trap for a selected microscopic particle, but insufficient to cause Raman scattering. In certain embodiments, the first and third power levels can be approximately equal, i.e., a preset power level may be used for both levels. The laser beam can be provided by a diode laser, and can have a frequency between about 500 nm and about 1500 nm. Preferably, the first power level is between about 1.0 mW and about 5.0 mW. More preferably, the first power level is between about 1.0 mW and about 3.0 mW. Preferably, the second power level is between about 15.0 mW and about 30.0 mW. More preferably, the second power level is between about 5.0 mW and about 20.0 mW.

Without wishing to be bound by a single theory, it is believed that the photodamage to a microscopic particle can be minimized by using a first, lower power level to optically trap the microscopic particle and a second, higher power level to produce Raman scattering. A higher power level laser beam is needed to produce Raman scattering than is necessary to optically trap a particle. Thus, the exposure of the particle to the higher power level laser beam that is necessary to produce Raman scattering can be minimized by switching between at least two laser beam power levels: a first, lower power level for optical trapping, and a second, higher power level for producing Raman scattering.

Figure 3:
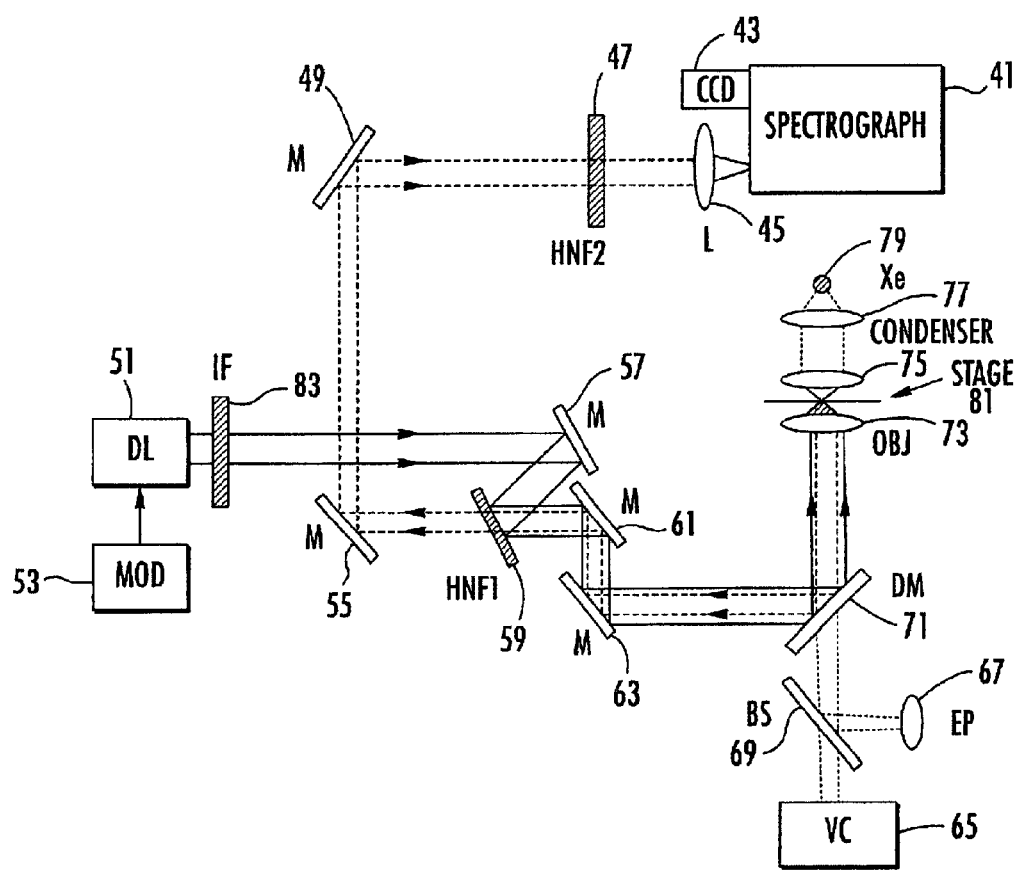
FIG. 3 is a schematic illustration of embodiments of laser tweezers/Raman spectroscopy systems according to embodiments of the present invention.

FIG. 3 is a schematic illustration of embodiments of laser tweezers/Raman spectroscopy systems according to embodiments of the present invention. The microscopic particle 81 is placed in a sample container (not shown) and immersed in a fluid medium. A diode laser 51 produces an elliptical near infrared (NIR), 785 nm beam that is converted to a circular beam with an anamorphic prism pair (not shown). The diode laser shown is commercially available under the name HL7852 (Hitachi America, Dallas, Tex., U.S.A.). The diode laser is temperature stabilized (within 0.01° C.) so that the line-width of the single-mode output is maintained within a few tens of megahertz, and so that the long-term frequency drift is minimized. Y. Q. Li, W. H. Burkett, and M Xiao, Pot. Lett. 21, 982 (1996).

The circular beam is spectrally filtered by an interference filter 83 and then introduced into an inverted microscope (not shown) equipped with an objective (100×; N.A., 1.25) to form a single-beam optical trap. The laser spot size at the focus is approximately 1–2 µm, and the microscopic particle 81 is captured and held approximately 10–15 µm above the bottom cover plate of the sample container (not shown). The laser beam from the diode laser 51 is reflected by mirror 57 to holographic notch filter 59. The holographic notch filter 59 is commercially available under the name HNPF-785AR (Kaiser Optical Systems, Ann Arbor, Mich., U.S.A.). The holographic notch filter 59 is used as a dichroic beam splitter that reflects the 785 nm excitation laser beam at an incident angle of 18°, and transmits the Raman signals above 810 nm. The holographic notch filter 59 reflects the laser beam to mirrors 61 and 63 and to dichroic mirror 71. The dichroic mirror 71 reflects the laser beam to lens 73, which focuses the laser beam onto the sample microscopic particle.

The laser beam initially is preferably transmitted at a first, lower power level that is sufficient to optically trap the microscopic particle 81. However, the first power level is preferably insufficient to excite the microscopic particle 81 to produce a Raman spectrum, i.e., enough Raman scattered light for an adequate, identifiable Raman spectrum. A modulator 53 such as a pulse generator is used to modulate the driving current and thus to increase the laser power level to produce Raman scattering. Y. Q. Li, W. H. Burkett, and M. Xiao, Opt. Lett. 21, 982 (1996).

The laser beam produced at the second, higher power level follows the path described above. As would be understood by one of skill in the art, both Raman and Rayleigh scattered light can be produced. Raman and Rayleigh scattered light from the microscopic particle 81 is collimated with lens 73 and reflected from dichroic mirror 71 to mirrors 61 and 63. The holographic notch filter 59, which reflects the laser beam as described above, transmits the Raman scattered light and removes a portion of the Rayleigh scattered light. The Raman scattered light and any remaining Rayleigh scattered light is reflected by mirrors 55 and 49 and passes through a second holographic notch filter 47. The second holographic notch filter 47 removes most of the remaining Rayleigh scattered light. The beam of Raman scattered light is then focused by lens 45 onto an entrance slit of an imaging spectrograph 41. The spectrograph is equipped with a liquid-nitrogen-cooled, front-illuminated charge coupled device (CCD) 43, such as a CCD imaging camera available under the commercial name SPECTRUM ONE™ (Instruments SA, Edison, N.J., U.S.A.).

In the embodiments depicted in FIG. 3, green filtered Xenon (Xe) illumination lamp 79 produces light that passes through lenses 77 and 75 and is focused on the microscopic particle 81. Light from the green-filtered xenon illumination light 79 illuminates the sample microscopic particle 81. The dichroic mirror 71 transmits the green-filtered illumination light to the inverted microscope (not shown). The inverted microscope includes a video camera 65 for recording a view of the sample and an eyepiece 67 for viewing the sample in real time. The video camera 65 and inverted microscope system are used for observation and for recording optical images of trapped particles.

The laser beam frequency and parameters of the holographic notch filters 47, 59 are matched as would be understood by one of skill in the art. The selection of dichroic mirror 71 as well as other elements and configurations in the embodiments depicted in FIG. 3 may be adjusted according to known techniques.

Figure 12:
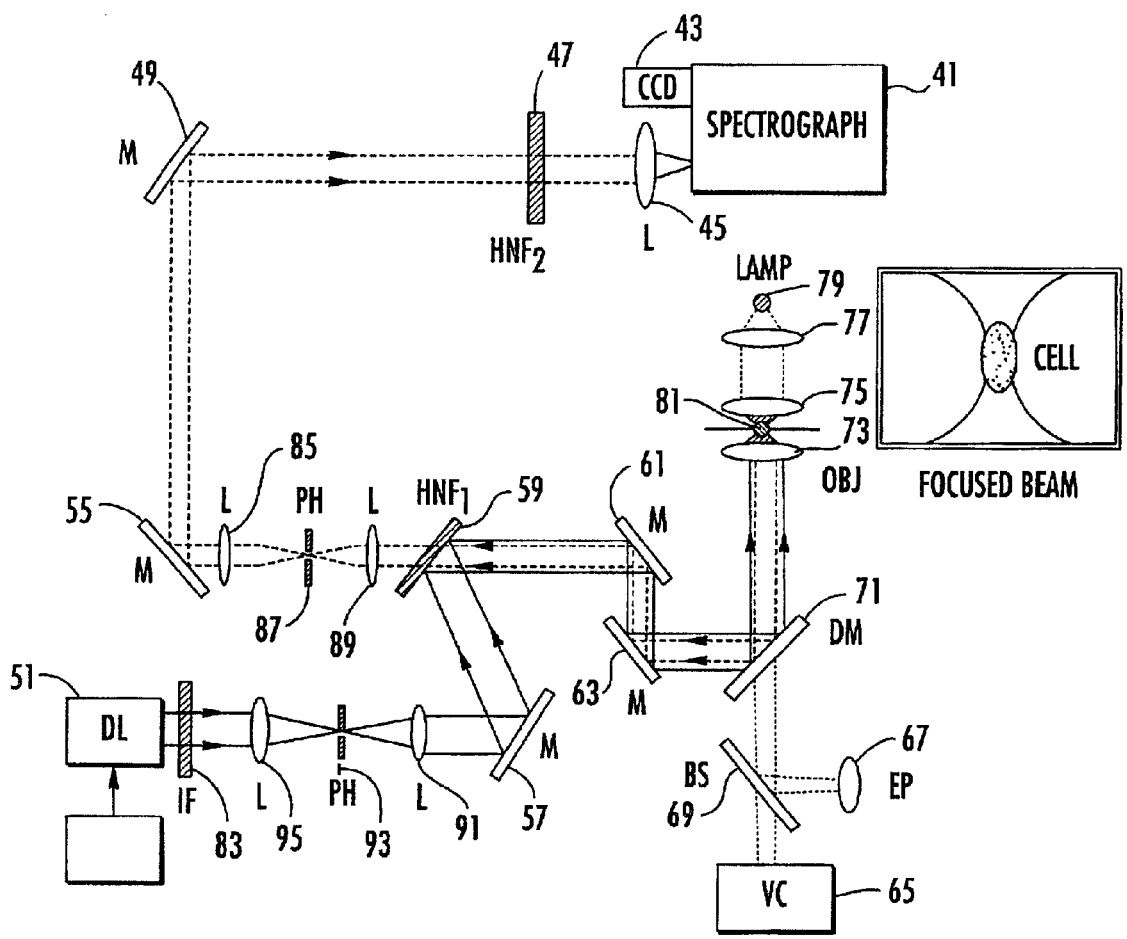
FIG. 12 is a schematic illustration of embodiments of laser tweezers/Raman spectroscopy systems according to embodiments of the present invention.

FIG. 12 is another schematic illustration of embodiments of laser tweezers/Raman spectroscopy systems according to embodiments of the present invention. The system shown in FIG. 12 operates similarly to the system shown in FIG. 3. However, the system shown in FIG. 12 includes a confocal configuration that can reduce stray light background using a pinhole aperture. Other configurations, spectroscopy techniques and optical trapping techniques known to those of skill in the art may be employed.

With reference to FIG. 12, the microscopic particle 81 is placed in a sample container (not shown) and immersed in a fluid medium. A diode laser 51 produces a laser beam that is spectrally filtered by an interference filter 83 and then introduced into an inverted microscope (not shown) equipped with an objective (100×; N.A., 1.25) to form a single-beam optical trap.

The laser beam from the diode laser 51 is focused onto pinhole aperture 93 by lens 95 and subsequently collimated by lens 91. The laser beam is reflected by mirror 57 to holographic notch filter 59. The holographic notch filter 59 is used as a dichroic beam splitter that reflects the 785 nm excitation laser beam at an incident angle of 18°, and transmits the Raman signals above 810 nm. The holographic notch filter 59 reflects the laser beam to mirrors 61 and 63 and to dichroic mirror 71. The dichroic mirror 71 reflects the laser beam to lens 73, which focuses the laser beam onto the sample microscopic particle.

The laser beam can be transmitted at a first, lower power level that is sufficient to optically trap the microscopic particle 81. However, the first power level is preferably insufficient to excite the microscopic particle 81 and produce Raman scattering. The modulator 53 increases the power of the laser beam to a second power level to produce Raman scattering.

The laser beam produced at the second, higher power level follows the path described above. The resulting Raman and Rayleigh scattered light from the microscopic particle 81 is collimated with lens 73 and reflected from dichroic mirror 71 to mirrors 61 and 63. The holographic notch filter 59, which reflects the laser beam as described above, transmits the Raman scattered light and removes a portion of the Rayleigh scattered light. Lens 89 focuses the light onto pinhole aperture 87. The light that passes through pinhole aperture 87 is collimated by lens 85. Pinhole apertures 87 and 93 are preferably 200 μm confocal pinhole apertures, which reject most of the off-focusing Rayleigh scattered light.

The Raman scattered light and any remaining Rayleigh scattered light is reflected by mirrors 55 and 49 and passes through a second holographic notch filter 47. The second holographic notch filter 47 removes most of the remaining Rayleigh scattered light. The beam of Raman scattered light is then focused by lens 45 onto an entrance slit of an imaging spectrograph 41. The spectrograph is equipped with CCD 43.

Green filtered Xenon (Xe) illumination lamp 79 produces light that passes through lenses 77 and 75 and is focused on the microscopic particle 81. Light from the green-filtered xenon illumination light 79 illuminates the sample microscopic particle 81. The dichroic mirror 71 transmits the green-filtered illumination light to the inverted microscope (not shown). The inverted microscope includes a video camera 65 and an eyepiece 67.

The following Examples are provided to illustrate the present invention, and should not be construed as limiting thereof.

In Examples 1–2, the LTRS system described in FIG. 3 was used. Unless otherwise stated, the particle is trapped when the diode laser 51 is programmed to operate at a low power level (about 2.0 mW at the sample). When a Raman measurement was taken, the laser power is increased (up to about 20 mW) for a short period of time (typically about 2.0 s for CCD acquisition) to ensure high excitation intensity. After the spectrum was taken, the laser returns to low-power operation for optical trapping.

EXAMPLE 1

Figure 4:
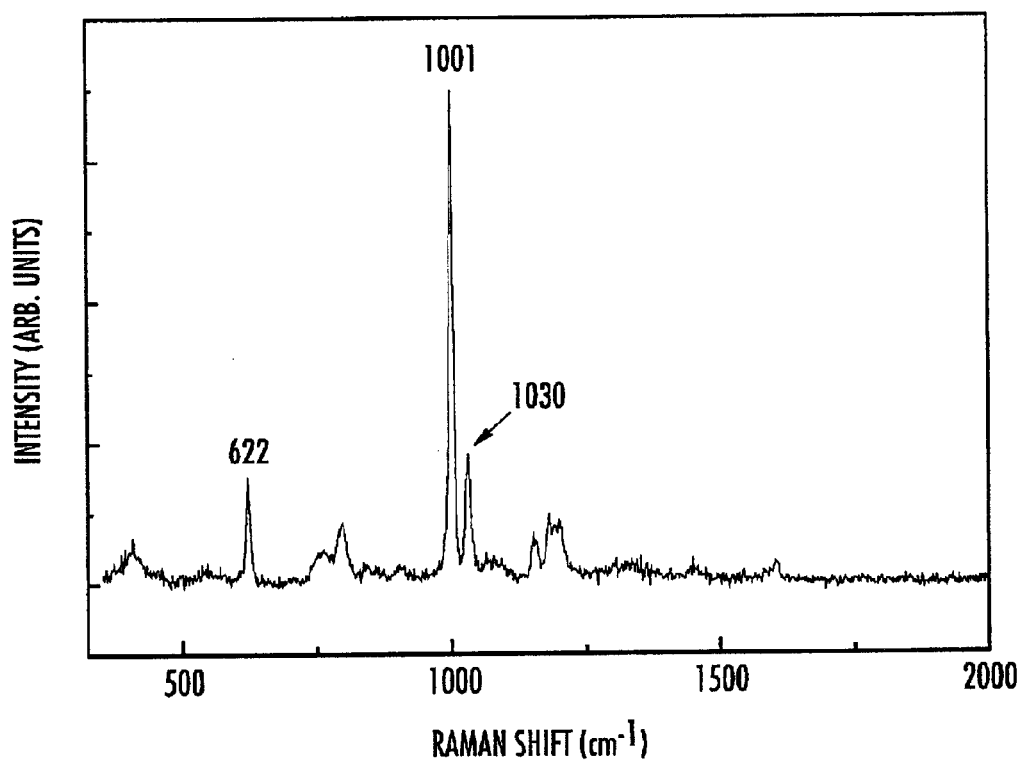
FIG. 4 is a Raman spectrum of a single polystyrene latex bead of 2.03 $\mu$m diameter in an optical trap.
Figure 5:
FIG. 5 is an image of a single polystyrene latex bead of 2.03 $\mu$m diameter in an optical trap.

A polystyrene bead of 2.03 μm diameter (obtained from Bangs Laboratories, Technology Drive Fishers, IN, U.S.A.), suspended in water was used for calibration and alignment of the LTRS system described in FIG. 3. FIG. 4 shows the Raman spectrum of a trapped polystyrene bead with a CCD integration time of 2.0 seconds and a 600-g mm$^{-1}$ spectrograph grating. FIG. 5 is an image of a single polystyrene latex bead of 2.03-μm diameter in an optical trap observed with the video camera 65. The background noise was recorded without the trapped bead under the same acquisition time and height conditions and was subtracted from the spectra shown in FIG. 4. The observed bands of Raman signal appear identical to those of published spectra obtained without using the power-switching scheme described above, and the observed linewidth of the 1001 cm$^{-1}$ band illustrates that the Raman shift resolution of the LTRS system is better than 8 cm$^{-1}$.

Figure 6:
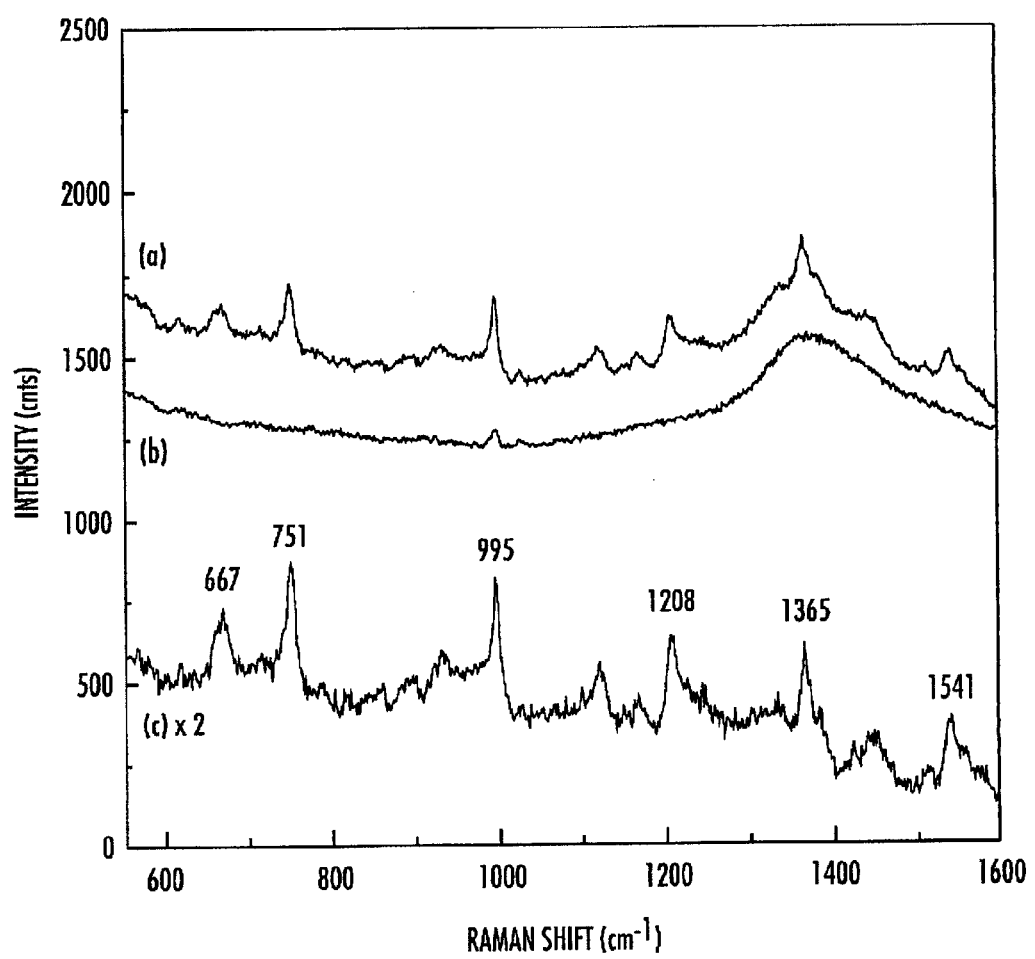
FIG. 6 is graph of a Raman spectra of a single red blood cell in a saline solution.
Figure 7:
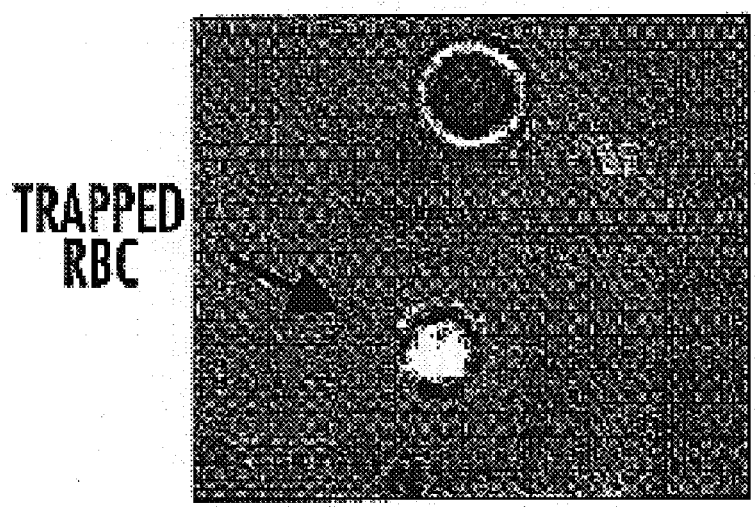
FIG. 7 is an image of a single red blood cell in a saline solution.

FIG. 6 is graph of a Raman spectra of a single red blood cell in a saline solution. A fresh blood sample obtained from a healthy volunteer was diluted to 1:10000 with 0.9% saline solution. A cell typically drifts at a speed of a few micrometers per second in the bulk solution before it sticks to the bottom cover plate. Once the cell is captured in the trap, its movement range is less than 300 nm. FIG. 7 is an image of a single red blood cell in a saline solution that was held about 15 μm above the bottom plate of the container. The Raman spectrum shown in FIG. 6 was recorded with an exposure time of 5.0 s and an excitation of 20 mW, and the trapping power was kept at 2.0 mW. Curve A is the spectrum recorded from a trapped red blood cell. Curve B is the background spectrum without a red blood cell in the trap under the same acquisition conditions. Curve C is the Raman spectrum after background subtraction.

Several characteristic bands are observed in FIG. 6 at 667 cm$^{-1}$ [$v_7$ haem], 751 cm$^{-1}$ [$v_{14}$ haem vibration], 995 cm$^{-1}$ [$6(C_\delta C_I)$], 1365 cm$^{-1}$ [$v_4(C_\alpha N)$] and 1541 cm$^{-1}$ [$v_{11}(C_\beta C_\beta)$] and appear identical to the assigned and published bands. B. R. Wood, B. Tait, and D. McNaughton, Biochim. Biophys. Acta 1539, 58 (2001). It is believed that because the excitation size (about 2 μm) is smaller than the cell size (about 7 μm), the spectra collected from the trapped red blood cell comes from a part of the cell rather than the entire cell. The characteristic bands from the trapped red blood cell did not change significantly during thirty minutes of trapping time at the low power trapping power level of about 2.0 mW, during which Raman spectra at the 20 mW power level was periodically taken. However, if the cell was trapped and excited with a cw laser of 20 mW, the characteristic bands shown in FIG. 6 disappeared after about 15 minutes. It is believed that the bands disappeared because of photodamage to the red blood cell at the higher energy level.

EXAMPLE 2

Figure 8:
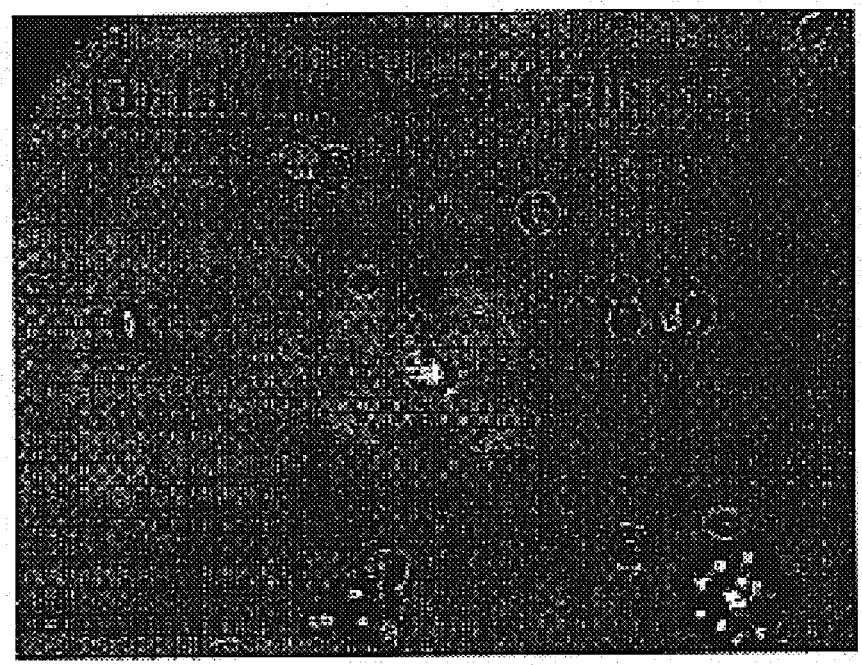
FIG. 8 is an image of a single living yeast cell in a solution.
Figure 10:
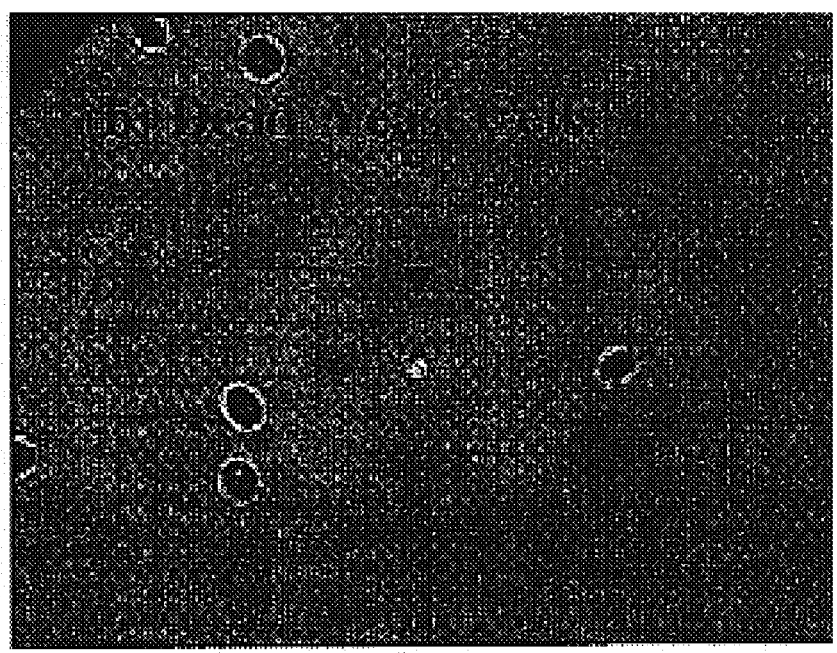
FIG. 10 is an image of a single dead yeast cell in a solution.

NIR Raman spectroscopy can also be used to identify the physiological states of single cells in an optical trap without requiring the use of staining techniques because the identification is done in real time. FIG. 8 is an image of a single living yeast cell in a solution, and FIG. 10 is an image of a single dead yeast cell in a solution. The living yeast cells were obtained from Hubbard Scientific (Northbrook, Ill., U.S.A.). And were cultured in a yeast solution prepared at a concentration of 40 g/L at room temperature. The dead yeast cells were prepared by sinking a tube of living yeast cell solution in a boiling water bath for 10 minutes and then gradually cooling the tube to room temperature. From the images in FIGS. 8 and 10, it appears difficult or impossible to clearly distinguish the living cells from the dead cells when the cells are unstained, although the living cells may appear slightly more transparent than the dead cells.

Figure 9:
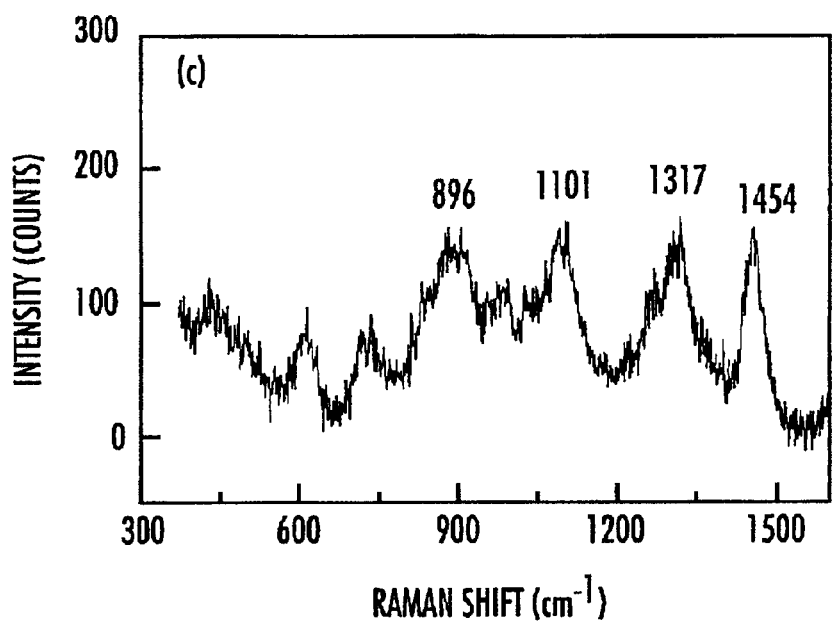
FIG. 9 is graph of a Raman spectra of a single living yeast cell in a solution.
Figure 11:
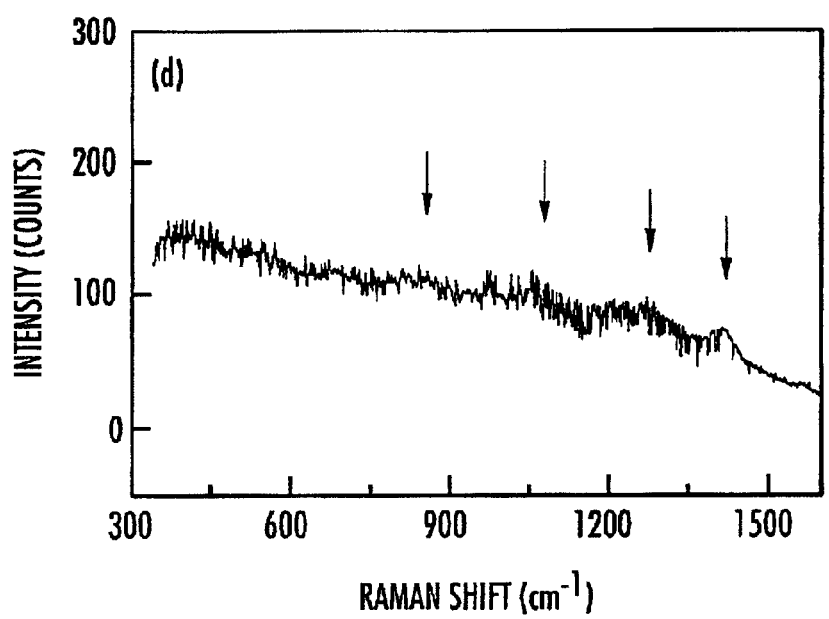
FIG. 11 is graph of a Raman spectra of a single dead yeast cell in a solution.

FIG. 9 is graph of Raman spectra of a single living yeast cell in a solution with four characteristic bands: 896 cm$^{-1}$, 1101 cm$^{-1}$, 1317 cm$^{-1}$, and 1454 cm$^{-1}$. FIG. 11 is graph of Raman spectra of a single dead yeast cell in a solution obtained in the same exposure (5.0 s) and excitation (20 mW) conditions for a trapped dead yeast cell. The characteristic bands shown in FIG. 9 for a living yeast cell do not appear for the dead yeast cell spectrum shown in FIG. 11. The scattering background for the dead yeast cell in FIG. 11 at low-frequency shifts is increased compared to the live yeast cell spectrum in FIG. 9.

The results depicted in FIGS. 9 and 11 illustrate that the boiling water likely killed the yeast cells and changed its histology and molecular configuration. It was observed that a trapped yeast cell remained alive for more than 30 minutes at the low trapping power of 2.0 mW.

EXAMPLE 3

In Example 3, the LTRS system described in FIG. 12 was used. Unless otherwise stated, a semiconductor diode laser at near 785 nm was used for both trapping and Raman excitation of a living cell in solution. The laser spot size at the focus is about 2 $\mu$m and a single cell is captured and held about 15 $\mu$m above the bottom cover plate of the sample container. The diode laser is temperature-stabilized with a controller and the excitation wavelength can be conveniently shifted by tuning the temperature of the laser diode with a slope of about 0.3 nm/° C. while keeping the output power constant by controlling the driving current.

A low power NIR laser was chosen to reduce the absorption-induced degradation of the living cell and reduce the fluorescence interference on the single cell spectra, which is a severe problem with UV or visible excitation. F. Sureau, L. Chinsky, C. Amirand, J. P. Ballini, M. Duquesne, A. Laigle, P. Y. Turpin, and P. Vigny, Appl. Spectrosc. 44, 1047–1051 (1990). However, the background due to the residual fluorescence and the stray light is still much larger than a single-cell Raman spectrum. K. C. Schuster, E. Urlaub, J. R. Gapes, Journal of Microbiological Methods, 42 29–38 (2000). B. R. Wood, B. Tait, and D McNaughton, Biochimica et Biophysica Acta 1539, 58–70 (2001). J. G. Brennan III, Y. Wang, R. R. Dasari, and M. S. Feld, Appl. Spectrosc. 51, 201–208 (1997). Shifted excitation Raman difference spectroscopy (SERDS) technique was employed to remove the broad background. A. P. Shreve, N. G. Cherepy, and R. A. Mathies, Appl. Spectrosc. 46, 707–710 (1992). J. J. Baraga, M. S. Feld, and R. P. Rava, Appl. Spectrosc. 46, 187–711 (1992). P. A. Mosier-Boss, S. H. Lieberman, and R. Newbery, Appl. Spectrosc. 49,630–638 (1995). S. E. J. Bell, E. S. O. Bourguignon, and A. Dennis, Analyst, 123, 1729–1734 (1998). By slightly shifting diode laser frequencies, the broad background remains approximately unchanged while the sharply peaked Raman bands follow the shifted excitation frequency. Subtraction of the two spectra obtained with slightly shifted excitation frequencies gives a derivative-like spectrum from which the background has been effectively eliminated and Raman features can be extracted. The spectral resolution of the system is estimated to be about 8 cm$^{-1}$.

Single-cell Raman spectra can be improved by using the SERDS technique. With a laser excitation frequency L, the measured spectrum for a single cell can be expressed as $$S_m(v) = [L_{RS}(v) + L_F(v)]R(v) + B(v), \qquad (1)$$

where $L_{RS}(v)$ represents the actual single cell Raman spectrum, $L_F(v)$ is the fluorescence spectrum from the molecules inside the cell, B(v) is the stray light line shape accounting for unfocused light that is scattered from collection lenses, filters, and mirrors and enters the spectrograph. J. F. Brennan III, Y. Wang, R. R. Dasari, and M. S. Feld, Appl. Spectrosc. 51, 201–208 (1997). For a trapped single cell, the stray light is dominated by Rayleigh-scattered laser light. With a slightly shifted excitation frequency $v_L + \delta v_L$, the Raman bands $L_{RS}(v)$ follows the frequency shift while the broad $L_F(v)$, R(v), and B(v) remain nearly unchanged and the measured spectrum is $S'_m(v) = [L_{RS}(v + +L_F(v)]R(v) + B(v)$. So, the fluorescence and stray light background can be removed from the spectral-calibrated difference spectrum, $S_d(v) = (S_m(v) - S'_m(v))/R(v) = L_{RS}(v) - L_{RS}(V + \delta v_L)$, which is derivative-like Raman spectrum. The difference spectrum $S_d(v)$ can be curve-fitted with N-double Lorentzian bands of the type $$S(v) = \sum_{i=1}^{N} \left[ \frac{H_i \sigma_i^2}{\sigma_i^2 + (v - v_i)^2} - \frac{H_i \sigma_i^2}{\sigma_i^2 + (v - v_i + \sigma v_L)^2} \right]. \qquad (2)$$

P. A. Mosier-Boss, S. H. Lieberman, and R. Newbery, Appl. Spectrosc. 49, 630–638 (1995). The curve fitting with Eq.(2) gives the peak frequency $v_i$, height $H_i$, and width $\sigma_i$ for each band and these parameters are used to reconstruct the conventional Raman spectrum $L_{RS}(i)$.

The SERDS technique effectively removes the strong background and yields high quality single-cell Raman spectra. This method can be used to study highly scattered cells, such as single heat-killed yeast cells. In experiments where yeast cells were treated with boiling water for about 10 min, the conformation of yeast cells was changed. For example, the proteins in the heat-treated cells have been denatured.

Figure 13:
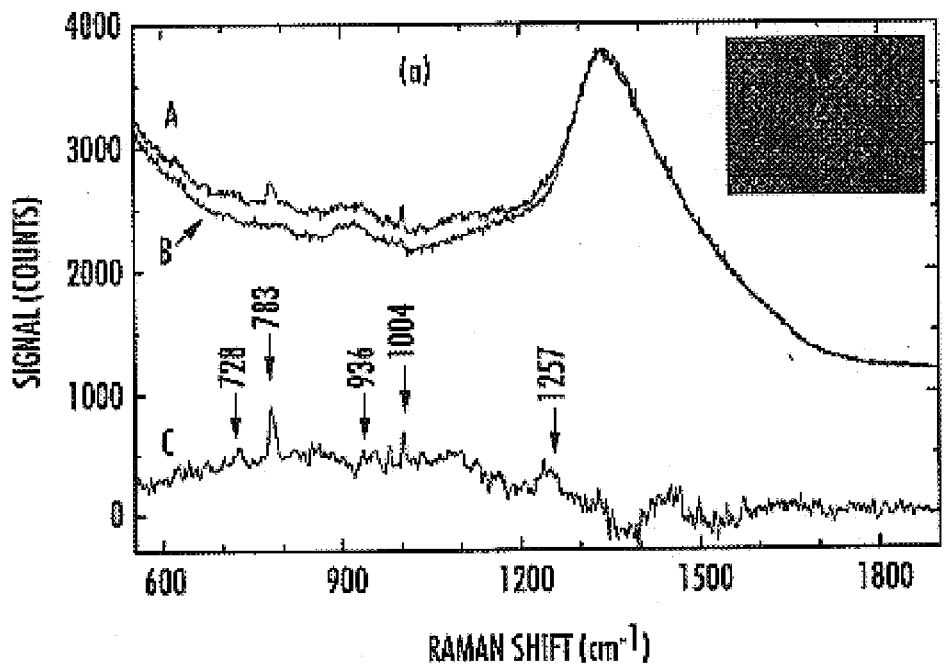
FIG. 13 is graph of a Raman spectra of a single E. Coli bacterium adsorbed on a glass cover plate.
Figure 14:
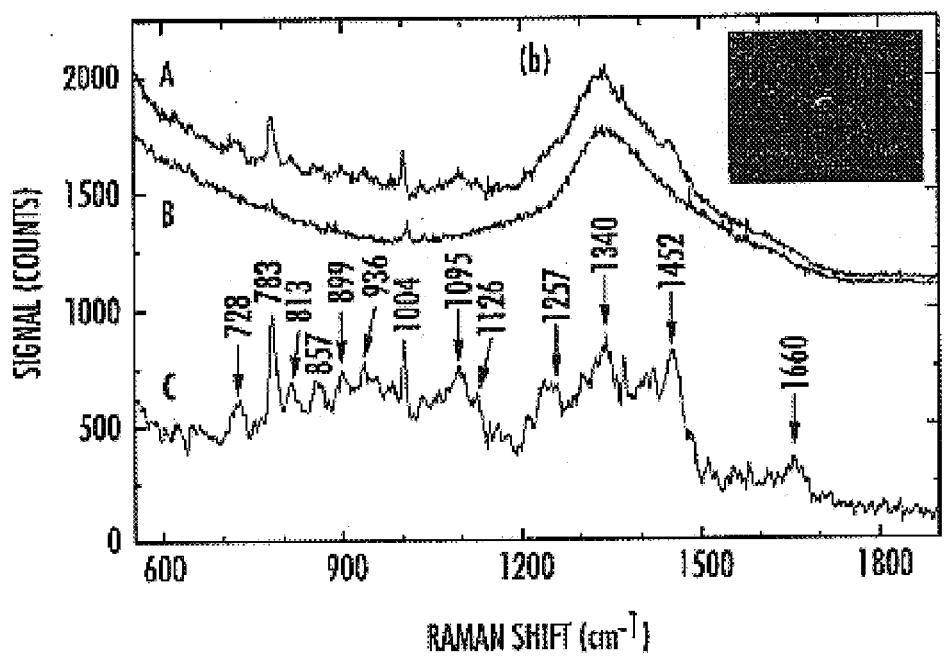
FIG. 14 is graph of a Raman spectra of a single E. Coli bacterium optically trapped above a cover plate in solution.

FIG. 13 is graph of a Raman spectra of a single E. Coli bacterium adsorbed on a glass cover plate. FIG. 14 is graph of a Raman spectra of a single E. Coli bacterium optically trapped above a cover plate in solution. The inset images in FIGS. 13 and 14 are images of the E. Coli bacterium for which the respective spectra were taken. Improved signal-to-noise ratio is obtained for the trapped cell compared to that for the immobilized cell. The living E. Coli bacteria were grown in a 500 ml glass culture bottle and incubated at 35° C. with agitation of the cell bath to prevent deposition of cells on the flask. A drop of fresh cell suspensions was then diluted with low background (LB) solution so that only a few cells appear on the view field of the microscope. The living E. Coli bacteria have a cylinder wall with a length of between about 2 and about 3 μm. Some of the E. Coli bacteria move rapidly in solution. Once the cell is captured in the optical trap, the long side of the cell is re-aligned to be parallel to the laser propagation direction. This alignment is observed because the longitudinal trapping force is weaker than the transverse force. M. P. Sheetz, ed., *Laser Tweezers in Cell biology*, Vol. 55, Methods in Cell Biology (Academic Press, Sandiego, Calif., 1998). The captured cell automatically locates in the confocal excitation position, independent of the mechanical instabilities of the table and the microscope because the cell migrates to the center of the optical trap.

The entired volume of the captured E. Coli cell is excited with the trapping beam when the power level of the laser beam is increased to produce Raman spectra. Curve A in FIG. 14 is the spectrum recorded when an E. Coli cell is trapped about 15 μm above the bottom plate. The spectrum shown in FIGS. 13 and 14 were taken with an acquisition time of 60 s and a 15 mW excitation power level with an estimated intensity of 0.4 MW/cm² at 785 nm.

In both FIGS. 13 and 14, Curve A is the spectrum recorded from the cell. Curve B is the background spectrum without the cell in the trap and Curve C is the subtraction spectrum (Curve A-Curve B). The subtracted spectrum was calibrated with the system spectral response (R(v)) and magnified by a factor of two for display. The R(v) was determined with a National Institute of Standards and Technology (NIST) calibrated fiber light source placed at the sample position in the microscope. The measured source spectrum is equal to the following equation:

$$R(v) = W_m(v)/W_k(v)$$

Where $W_m$ is the measured source spectrum and $W_k$ is the known spectrum of the calibrated source. J. G. Brennan III, Y. Wang, R. R. Dasari, and M. S. Feld, Appl. Spectrosc. 51, 201–208 (1997).

The background Curve B for the plate-immobilized cell in FIG. 14 is about three times larger than the signal for the trapped cell in FIG. 13. Therefore, some weak peaks were not observed in the immobilized cell in FIG. 14. Table 1 shows the observed Raman bands of a single trapped E. Coli cell and the tentative assignation, from which the nucleic acids (C, T) band at 783 cm⁻¹, the protein (phenylalanine) band at 1004 cm⁻¹ and other bands are observed.

TABLE 1

Raman bands of single *E. Coli* cells and tentative assignation

| Bands (cm⁻¹) | Assigned to |
|---|---|
| 1660 | Amide I |
| 1425 | Lipids (CH² bending) |
| 1340 | Nucleic acids (A, G) |
| 1259 | Amide III |
| 1126 | C-N |
| 1095 | DNA: O-P-O⁻ |
| 1004 | Phenylalanine |
| 936 | DNA: BK |
| 899 | DNA: BK |
| 783 | Nucleic acids (C, T) |
| 728 | Adenine |

Figure 15:
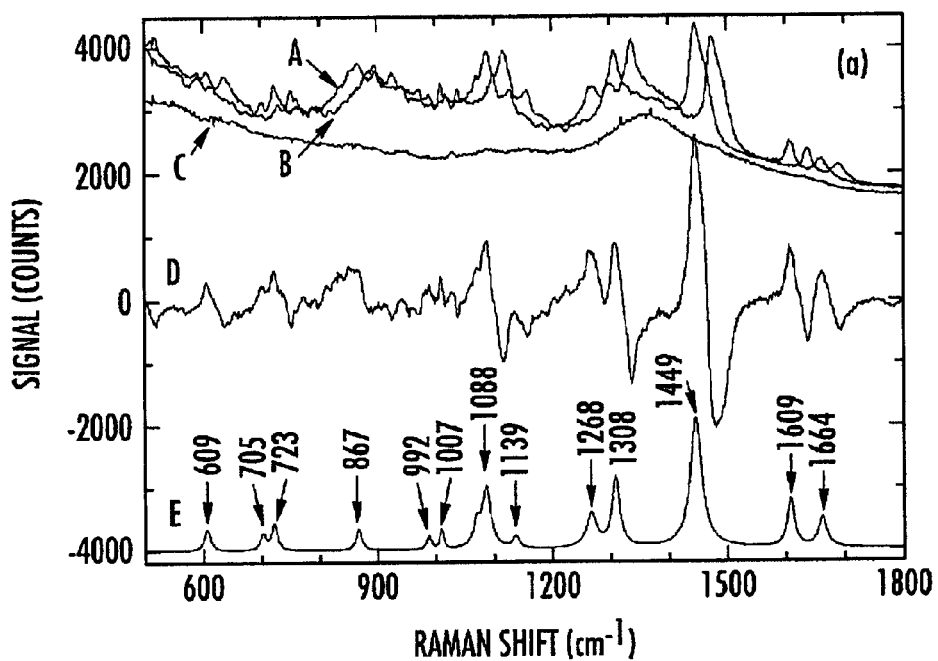
FIG. 15 is a graph of various Raman spectra of a single living yeast cell optically trapped in water.
Figure 16:
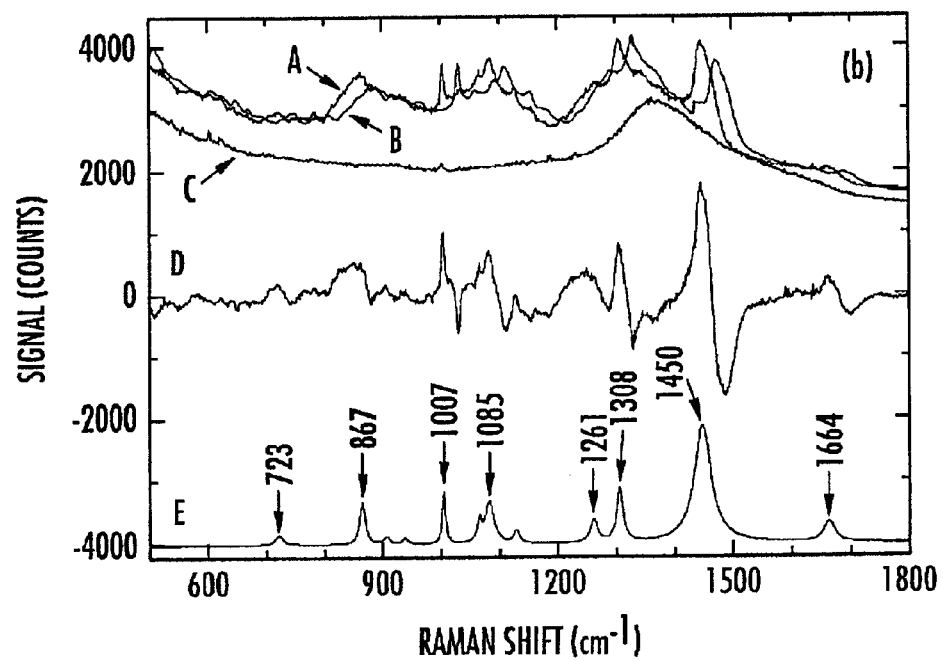
FIG. 16 is a graph of various Raman spectra of a single dead yeast cell optically trapped in water.

FIG. 15 is a graph of various Raman spectra of a single living yeast cell optically trapped in water and FIG. 16 is a graph of various Raman spectra of a single, floating unstained heat-treated yeast cell optically trapped in water. Table 2 shows the molecular assignment for the observed Raman bands.

TABLE 2

Raman bands of single yeast cells and tentative assignation

| Band (cm⁻¹) | Assigned to |
|---|---|
| 1659 | Amide I |
| 1609 | Tyrosine, Phenylalanine |
| 1450 | Lipids |
| 1308 | Amide III (deformed) |
| 1268 | Amide III, Adenini |
| 1088 | DNA: O-P-O⁻ |
| 1007 | Phenylalanine |
| 723 | Adenine |
| 609 | Phenylalanine |

A comparison of FIGS. 15 and 16 reveals that the Raman bands at 1609 cm⁻¹ and 609 cm⁻¹ are not present for the heat-treated yeast cell, while the 1007 cm⁻¹ band appears enlarged compared to the single living yeast cell. It is believed that these bands are related to phenylalanine (Phe) molecules inside the yeast cell. The disappearance of the Raman bands at 1609 cm⁻¹ and 609 cm⁻¹ and the enlargement of the 1007 cm⁻¹ band in the heat-treated cell may indicate a significant change in the Phe molecules in the composition of the heat-treated yeast cells. It is possible that the apparent change in Phe binding may be caused by a change in Phe binding conditions in denatured proteins.

Other information about cell structure may be inferred from the Raman spectra. For example, the living, optically trapped E. Coli cell Raman spectra in FIG. 14 reveals a relatively strong nucleic acid band at 783 cm⁻¹ (see also Table 1) and a relatively weak lipid band at 1452 cm⁻¹. The relative strength of the nucleic acid band and lipid band is consistent with the E. Coli structure. E. Coli cells have a relatively thin membrane and carry large amounts of nucleic acids. On the other hand, the Raman spectrum for a living yeast cell shown in FIG. 15 reveals a relatively strong lipid band at 1452 cm⁻¹ (see also Table 2). It is believed that yeast cells have a thick membrane, which may explain the observed strong lipid band.

EXAMPLE 4

Figure 17A:
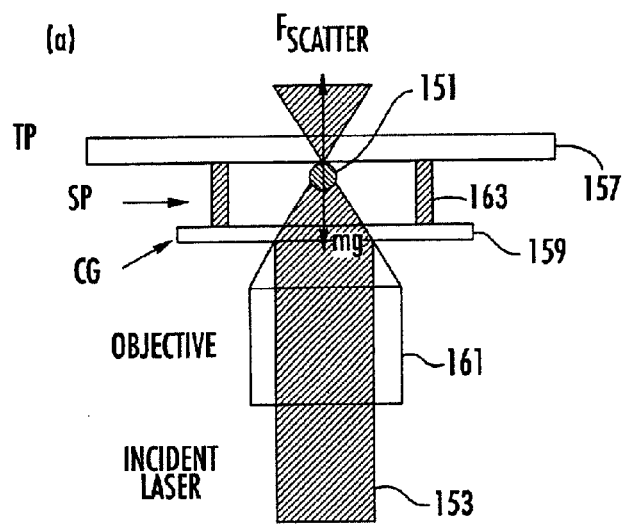
FIGS. 17A–C are schematic drawings illustrating optical trapping of a non-transparent particle by a laser focused near the top of the particle.
Figure 17B:
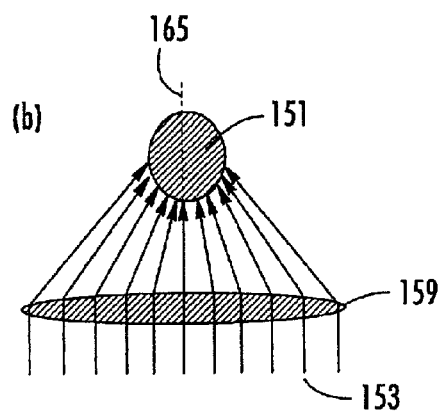
Figure 17C:
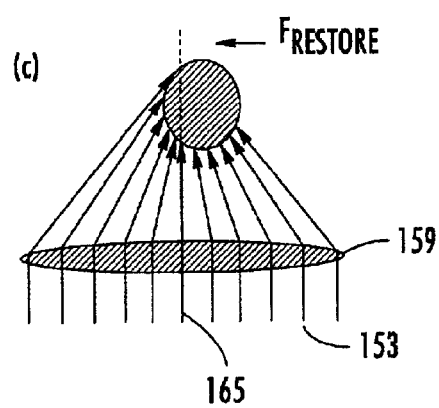

The mechanism of optical trapping of a non-transparent particle with a Gaussian beam is depicted in FIGS. 17A–C, which are schematic drawings illustrating optical trapping of a non-transparent particle by a laser focused near the top of the particle. With reference to FIG. 17A, the non-transparent particle 151 is held in a container that includes a top glass slide 157 and a cover glass 159 separated by a spacer 163. The non-transparent particle 151 absorbs the incident light rays from the beam 153 in essentially all directions. A repulsive force $F_{scatter}$ caused by the absorption pushes the particle in the direction of the beam 153. As shown in FIG. 17B, if the focus of the beam 153 is located near the top of the particle 151 and the particle 151 is symmetrically located in the beam axis 165, the net repulsive force in the transverse direction will be zero. If the particle 151 is shifted to the right of the beam axis due to the Brownian motion, as shown in FIG. 17C, the light flux absorbed by the sphere area in the right-hand side of the beam axis 165 is larger than that in the left-hand side. The repulsive force from the right-hand side is then larger than from the left hand side. Therefore, the net transverse repulsive force tends to pull the sphere toward the beam axis 165 if the sphere is located off-axis, acting as a restoring force $F_{restore}$. Shunichi Sato, Yasunori Harada, and Yoshio Waseda, Opt. Lett. 19, 1807–1809 (1994). In either case and with reference to FIG. 17A, a net repulsive force $F_{scatter}$ in the axial direction pushes the particle 151 upward, and the particle 151 moves up until the top glass slide 157, wherein $F_{scatter}$ is equal to the sum of the gravitational force mg of the particle and the glass contact force. Therefore, a stable three-dimensional trap can be formed for the absorptive particles. A similar analysis shows that a stable optical trap can be formed for metal particles (A. T. O'Neil and M. H. Dadgett, Opt. Commun. 185, 139–143 (2000). Shunichi Sato, Yasunori Harada, and Yoshio Waseda, Opt. Lett. 19, 1807–1809 (1994).) and highly refractive particles if the beam focus is located near the top of the particle, that is, the beam focus is closer to the distal side of the particle with respect to the laser beam source than the proximal side of the particle.

The experimental arrangement for the following example is described in FIG. 12 (see also C. Xie, M. A. Dinno, and L. Q. Li, Opt. Lett. 27, 249–251 (2002).). In summary, a circularized beam from a diode laser 51 at near 785 nm is spatially filtered and then introduced in an inverted microscope equipped with an objective (100 X, NA-1.3) to form a single beam optical trap. The sample holder (not shown) includes a top glass slide, a spacer of 50 μm thickness, and a bottom cover glass. In this example, the particle 81 is a non-transparent particle, which can be selectively trapped under the top glass slide by the repulsive force with the beam focus is located near the top of the particle as described above. The backscattered light from the optically trapped particle 81 is collimated with an objective lens 73 and passes through a focusing lens 89, a confocal pinhole aperture 87, which in this case is a 200 μm confocal pinhole aperture, to reject most of the off-focusing Rayleigh scattering light. Two interference notch filters 59 and 47 are used to remove most of the on-focusing Rayleigh scattering light. The Raman scattering light is then focused onto the entrance slit of an imaging spectrograph 41 equipped with a liquid-nitrogen-cooled charged-coupled detector (CCD). An illumination lamp 79 and a video camera system 65 are used to observe the image of the trapped particle. The spectral resolution of the LTRS system was estimated to be about 6 $cm^{-1}$ from the measured Raman bandwidth of a polystyrene bead.

In certain embodiments, the optical trap for the selected microscopic particle is formed with a laser beam at a first power level. The Raman scattering signals may be produced with the laser beam at a second power level. The second power level provides sufficient excitation energy to the selected microscopic particle to produce Raman scattering signals and the second power level is greater than the first power level. Alternatively, a single power level may be used for both optical trapping and Raman scattering.

Figure 18:
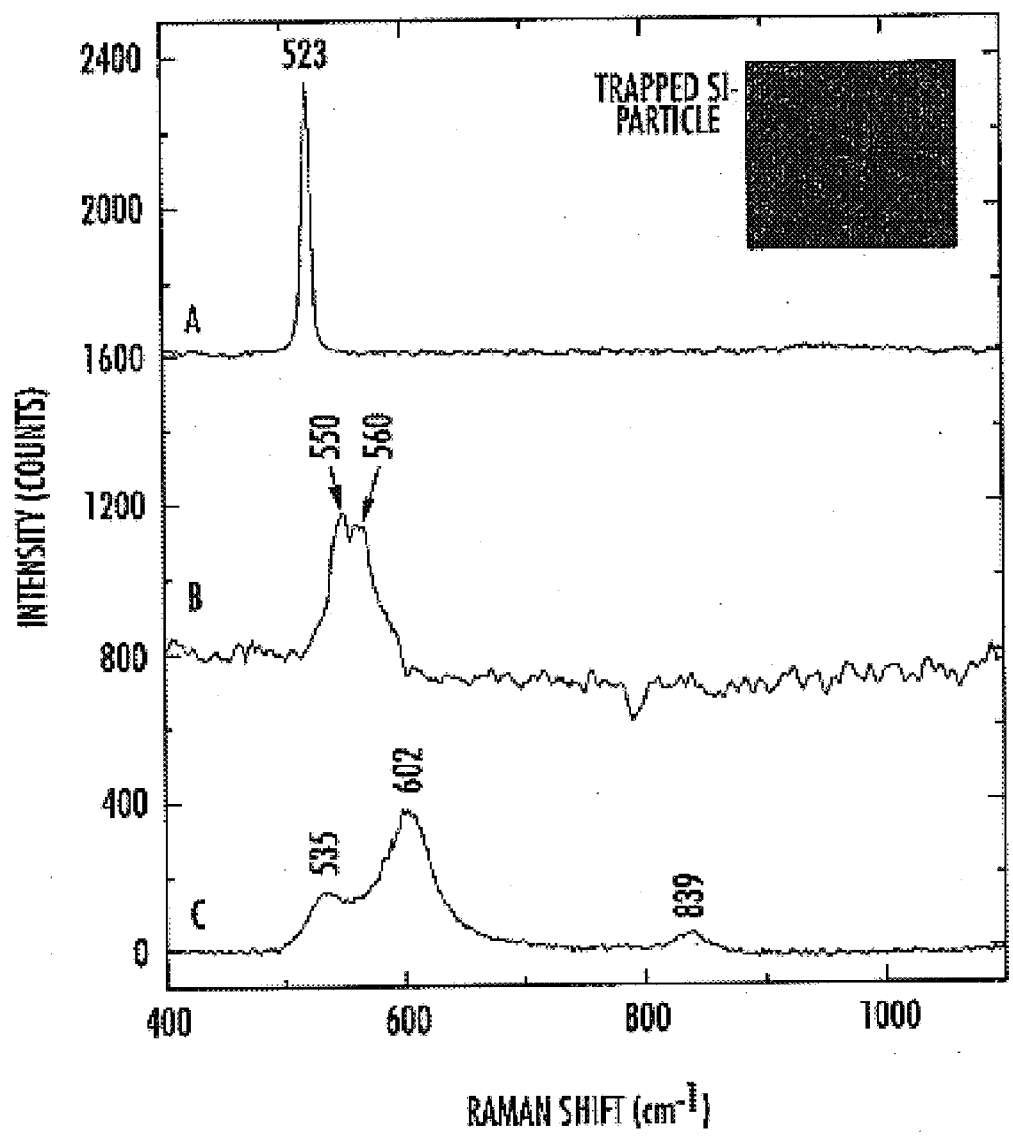
FIG. 18 is a graph of Raman spectra of various optically trapped particles having a high index of refraction, including a silicon crystal, a germanium particle, and a KnbO$_3$ crystal.

FIG. 18 is a graph of Raman spectra of various optically trapped particles having a high index of refraction, including a silicon crystal, a germanium particle, and a potassium niobate ($KnbO_3$) crystal, in water. Silicon, germanium, and potassium niobate ($KnbO_3$) micro-crystals are of importance in semiconductor and nonlinear optics manufacturing. Silicon, germanium, and potassium niobate ($KnbO_3$) have high indexes of refraction in visible-near infrared regions, e.g., an index of refraction (n) of about 3.4 for silicon, 4.0 for Germanium, and 2.3 for $KnbO_3$. The micro-crystals were prepared by grounding a piece of pure material into powder, and then diluting the powders with distilled water. The shape of the micro-crystals is irregular and the effective index (m) of the micro-crystals in water, which is defined as the index of the particle (n) divided by the index of the water ($n_b$=1.33), is too high to trap with single Gaussian beam tweezers. A. Ashkin, J. M. Dziedzie, J. E. Bjorkholm, and S. Chu, Opt. Lett, 11, 288–290 (1986). However, the particles can be trapped with the system described in FIG. 12 and FIGS. 17A–C.

Curve A in FIG. 18 is the Raman spectra observed from a trapped silicon particle of about 2 μm size, as shown in the inserted image. The typical integration time for Curve A and Curve B is 2 seconds with a laser power of 6 mW. The characteristic band at 523 $cm^{-1}$ is assigned to Si I phase. Y. G. Gogotsi and V. Domnich, S. N. Dub, A. Kailer and K. G. Nickel, Journal of Materials Research, 15, 871–879 (2000). Curve B is the Raman spectra from a trapped germanium particle. The observed Raman band near 560 $cm^{-1}$ is assigned to the Ge-C bond. L. Hoffmann, J. C. Bach, B. B. Nielsen, P. Leary, R. Jones, S. Öberg, Phys. Rev. B, 55, 11167–11173 (1997). Curve C is the Raman spectra from a trapped $KnbO_3$ particle, in which Raman bands at 535 $cm^{-1}$, 602 $cm^{-1}$, and 839 $cm^{-1}$ are observed. Curve C was obtained with a 30 second acquisition time and 16 mW incident power.

Figure 19:
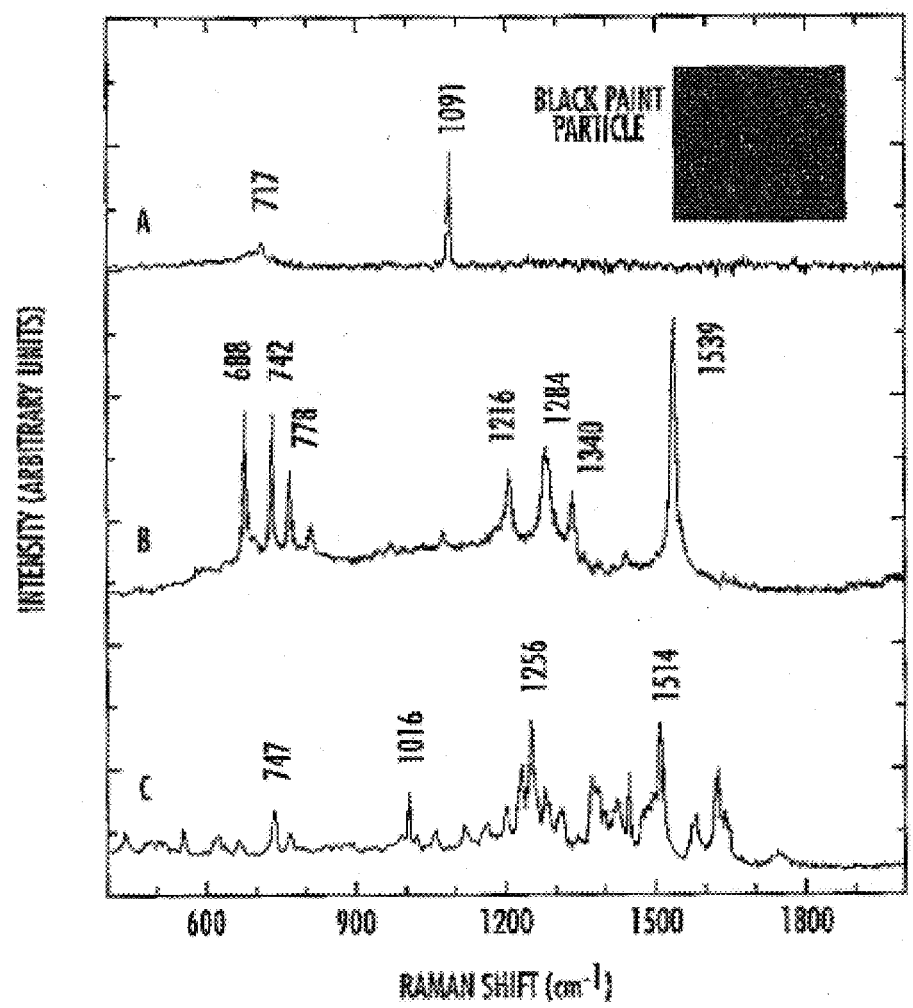
FIG. 19 is a graph of Raman spectra of single, optically trapped particles of absorptive color paints.

FIG. 19 is a graph of Raman spectra of single, optically trapped particles of absorptive color paints. The absorptive particles used to obtain the spectra were made of powders ground from a piece of dried black paint and other color paints that are often used for instrument and vehicle body painting. The size of the paint particles range from about 0.5 μm to about 10 μm with irregular shape. Curve A is the Raman spectra from a trapped black paint particle of about 2 μm size. The image of the trapped black paint particle is shown in the image insert. The black paint contains unknown materials that yield Raman bands at 1091 $cm^{-1}$ and 717 $cm^{-1}$. Curve B and Curve C are the Raman spectra from a trapped COLORPLACE™ paint particle (green color) and a trapped KRYLON™ paint particle (red color), respectively. For these measurements, the integration time was 10 seconds and the laser power was 6 mW. Although not all of the Raman bands were assigned to a particular composition because the molecular composition of the commercial painting materials is not known, the intrinsic difference in Raman spectra between different paint particles allows rapid identification of unknown paint particles. Therefore, the Raman spectra may be valuable, for example, in the recognition and identification of vehicles involved in car crashes and accidents.

Figure 20:
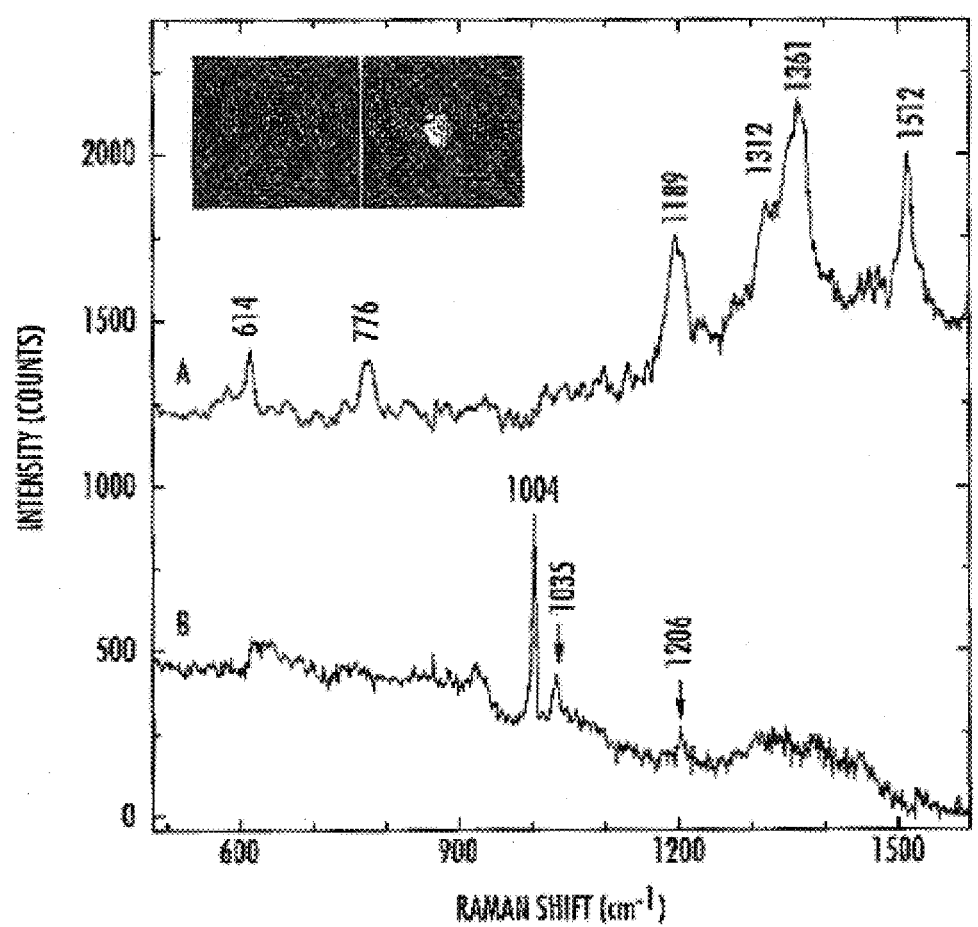
FIG. 20 is a graph of surface-enhanced Raman spectra of rhodamine 6G (R6G) (Curve A) and Phenylalanine (Phe) molecules (Curve B) observed from a trapped cluster of silver particles.

An LTRS system also allows trapping metal particles of micron size and enables observation of surface-enhanced Raman spectra of organic or biological molecules adsorbed on the surface of the trapped metal particle. FIG. 20 is a graph of surface-enhanced Raman spectra of R6G (Curve A) and Phenylalanine molecules (Curve B) adsorbed on the surfaces of single trapped silver clusters. The silver particles in water were prepared with a laser ablation method using a Yttrium Aluminum Garnet (YAG) pulsed laser (J. Neddersen, G. Chumanov, and T. M Cotton, Appl. Spectros., 47, 1959–1964 (1993).) and R6G or Phe solution of 1 μM concentration was added in the silver colloids for a one hour incubation. At this concentration, Raman spectra either from R6G or Phe bulk solution cannot be observed with an integration of 5 seconds and a laser power of 6 mW at 785 nm. However, as a clump of silver particles was trapped, Raman spectra from R6G (Curve A in FIG. 20) and Phe (Curve B in FIG. 20) were observed due to surface enhancement effect. "Surface enhancement" refers to the increased intensity of a Raman signal from a collection of molecules that are adsorbed on a metal surface. M. Fleischmann, P. J. Hendra and A. J. McQuillan, Chem Commun. 80 (1993).

The trapped silver particles were highly reflective, as shown by the insert images, where a low-pass filter was used to block the scattered laser line before entering the video camera. Specifically, image (a) is an image of the trapped silver cluster recorded with a short-pass filter and image (b) is the trapped silver cluster without the filter.

The observed characteristic bands of R6G at 614 cm$^{-1}$ (C-C-C ring in-plane bending), 776 cm$^{-1}$ (C-H out of plane bending), 1189 cm$^{-1}$ (C-H in-plane bending), 1361 cm$^{-1}$ (C–C stretching), and 1512 cm$^{-1}$ (C—C stretching) are the same as those of the published surface enhanced Raman scattering (SERS) spectra within the spectral resolution. G. Li, H. Li, Y. Mo, X. Huang and L. Chen, Chem. Phys. Lett., 330, 249–254 (2000). S. Nie, and S. R. Emory, Science, 275, 1102–1106 (1997). The characteristic bands at 1004 cm$^{-1}$ (aromatic ring) and 1035 cm$^{-1}$ were observed in the Raman spectra of Phe. It is noted that the trapped silver clusters were observed to randomly rotate inside the laser trap so that the surface enhancement effects were not as high as those observed in some literature.

In the drawings and specification, there have been disclosed typical preferred embodiments of the invention and, although specific terms are employed, they are used in a generic and descriptive sense only and not for purposes of limitation, the scope of the invention being set forth in the following claims. Moreover, various mirror configurations, filtering techniques, beam splitting techniques, optical traps involving more than one laser beam, and other spectroscopy and optical trapping techniques known to those of skill in the art may be used to accomplish the functions and features of the embodiments described herein.

What is claimed is:

1. A method for studying a selected microscopic particle comprising:

forming an optical trap for a selected microscopic particle with a laser beam at a first power level, the laser beam having a variable power level associated therewith;

increasing the variable power level associated with the laser beam to a second power level;

producing Raman scattering signals with the laser beam at the second power level, wherein the second power level provides sufficient excitation energy to the selected microscopic particle to produce Raman scattering signals and whereinthe second power level is greater than the first power level; and detecting a Raman spectrum from the Raman scattering signals produced by the laser beam at the second power level to thereby study the selected microscopic particle.

2. The method of claim 1, further comprising:

after detecting the Raman spectrum, decreasing the variable power level to a third power level, wherein the third power level provides sufficient power to form an optical trap.

3. The method of claim 2, wherein the third power level is approximately equal to the first power level.

4. The method of claim 1, wherein the first power level is insufficient to produce a Raman spectrum.

5. The method of claim 1, further comprising:

providing the laser beam with a diode laser.

6. The method of claim 1, wherein the laser beam has a frequency between about 500 and 1500 $\mu$m.

7. The method of claim 1, wherein the first power level is between about 1 mW and about 3 mW.

8. The method of claim 1, wherein the second power level is between about 15 mW and about 30 mW.

9. The method of claim 1, further comprising:

applying the laser beam at the second power level to the selected microscopic particle for a time sufficient to produce a Raman spectrum.

10. The method of claim 1, further comprising:

applying the laser beam at the second power level to the selected microscopic particle for about two seconds.

11. The method of claim 1, wherein the selected microscopic particle comprises a single biological cell.

12. The method of claim 11, wherein the biological cell is a living cell.

13. The method of claim 1, wherein the microscopic particle is unstained.

14. The method of claim 1, further comprising:

focusing the laser beam through a confocal aperture.

15. The method of claim 1, further comprising:

focusing the Raman scattering signals through a confocal aperture.

16. The method of claim 1, further comprising:

filtering the Raman scattering signals through a holographic notch filter.

17. A system for studying selected microscopic particles comprising:

a diode laser for producing a laser beam having at least a first and second power level, wherein the laser beam at the first power level is sufficient for optically trapping a selected microscopic particle immersed in an aqueous solution medium, wherein the second power level provides sufficient excitation energy to the selected microscopic particle to produce Reman scattering signals for a Reman spectrum, and wherein the second power level is greater than the first power level;

a beam splitter positioned to selectively direct the laser beam in a first direction and to selectively direct the Raman scattering signals radiating from the selected microscopic particle in a second direction;

a container for containing the selected microscopic particle immersed in the aqueous solution, wherein the container is positioned to receive the laser beam in the first direction; and a Raman spectrograph detector pbsitioned to receive the Raman scattering signals in the second direction.

18. The system of claim 17, wherein the first power level is insufficient to produce a Raman spectrum.

19. The system of claim 17, wherein the beam splitter reflects the laser beam from the diode laser in the first direction and transmits Raman scattering signals from the selected microscopic particle in the second direction.

20. The system of claim 17, wherein the laser beam has a frequency between about 500 and 1500 nm.

21. The system of claim 17, wherein the first power level is between about 1 and 3 nm.

22. The system of claim 17, wherein the second power level is between about 15 and about 30 nm.

23. The system of claim 17, wherein the second power level is applied to the selected microscopic particle for about two seconds.

24. The system of claim 17, wherein the selected microscopic particle comprises a single biological cell.

25. The system of claim 24, wherein the biological cell is a living cell.

26. The system of claim 17, wherein the microscopic particle is unstained.

27. The system of claim 17, further comprising:
a confocal aperture positioned to focus the Raman scattering signals.

28. The system of claim 17, further comprising:
a confocal aperture positioned to focus the laser beam.

29. The system of claim 17, further comprising:
a holographic notch filter positioned to filter the Raman scattering signals.

30. The system of claim 17, wherein the diode laser is configured for producing a laser beam having a power level of less than about 100 mW.

31. A method for studying selected microscopic particles comprising:
forming an optical trap with a laser beam at a first rower level for a selected microscopic particle, the selected microscopic particle having a proximal side and a distal side to a source of the laser beam;
focusing the beam near the distal side of the selected microscopic particle;
producing Raman scattering signals with the laser beam at a second power level, wherein the second power level provides sufficient excitation energy to the selected microscopic particle to produce Raman scattering signals and wherein the second power level is greater than the first power level; and
detecting a Raman spectrum from the Raman scattering signals produced by the laser beam.

32. The method according to claim 31, wherein the selected microscopic particle is non-transparent.

33. The method according to claim 31, wherein the laser beam is a Gaussian laser beam.

34. The method according to claim 31, wherein the selected microscopic particle comprises one or more organic or biological molecules adsorbed on the surface of a metal particle.

\* \* \* \* \*

UNITED STATES PATENT AND TRADEMARK OFFICE
CERTIFICATE OF CORRECTION

PATENT NO. : 6,897,950 B2
DATED : May 24, 2005
INVENTOR(S) : Li et al.

It is certified that error appears in the above-identified patent and that said Letters Patent is hereby corrected as shown below:

Title page,
Item [75], Inventors, include -- Changan Xie, Greenville, NC (US) --.
Item [56], References Cited, U.S. PATENT DOCUMENTS, include
-- 5,329,352    7/1994    Jacobsen    356/301 --.
OTHER PUBLICATIONS, include
-- Xie et al., "Near-infrared Raman spectroscopy of single optically trapped biological cells," OPTICS LETTERS, Vol. 27, No. 4, February 15, 2002, pp. 249-251.
International Search Report for PCT/US03/22700. --.

Column 15,
Line 46, should read -- nals and wherein the second power level is greater than --.
Line 63, should read -- frequency between about 500 and 1500 nm. --.

Column 16,
Lines 33-34, should read -- microscopic particle to produce Raman scattering signals for a Raman spectrum, and wherein the second --.
Line 45, should read -- a Raman spectrograph detector positioned to receive the --.

Column 17,
Line 15, should read -- forming an optical trap with a laser beam at a first power --.

Signed and Sealed this

Tenth Day of January, 2006

JON W. DUDAS
*Director of the United States Patent and Trademark Office*